United States Patent [19]

Okazaki et al.

[11] Patent Number: 4,656,279

[45] Date of Patent: Apr. 7, 1987

[54] PROCESS FOR PRODUCTION OF DECAHYDROISOQUINOLINE

[75] Inventors: Hiroshi Okazaki, Munakata; Mahito Soeda, Ongamachi; Hiromu Wada, Nishinomiya; Kiyotaka Onishi, Osaka, all of Japan

[73] Assignees: Nippon Steel Chemical Co., Ltd.; Iwatani Industrial Gases Corp., both of Tokyo, Japan

[21] Appl. No.: 685,090

[22] Filed: Dec. 21, 1984

[51] Int. Cl.$^4$ .......................................... C07D 217/02
[52] U.S. Cl. .................................................... 546/150
[58] Field of Search ........................................ 546/150

[56] References Cited

U.S. PATENT DOCUMENTS 3,205,278  9/1965  Lapporte ............................. 546/150
3,379,730  4/1968  Mathison ............................. 546/150

OTHER PUBLICATIONS

Kimoto et al., "Chem. Pharm. Bull.", Japan, vol. 10 (1962), pp. 362–365.

Grethe, *Isoquinolines*, Part One, 1981, John Wiley & Sons, New York, pp. 113–114.

Bernard Witkop, "Preparation of Cis- and Trans-Decahydroisoquinolines and of Bz- Tetrahydroisoquinoline", in the Journal of the American Chemical Society, vol. 70, No. 8, Sep. 1, 1984, pp. 2617–2619.

King et al, "Synthetic and Stereochemical Investigations of Reduced Cyclic Bases, Part IV, The Constitutions of the Exhaustive Methylation Products of Trans-Octahydro-N-Methyl-Indole and of Cis- and Trans-Decahydro-N-Methylisoquinoline", in the Journal of the Chemical Society, pp. 3798–3802 (1956).

*Primary Examiner*—Glennon H. Hollrah
*Assistant Examiner*—James H. Turnipseed
*Attorney, Agent, or Firm*—Armstrong, Nikaido, Marmelstein & Kubovcik

[57] ABSTRACT

A process for the production of decahydroisoquinoline is disclosed which comprises hydrogenating isoquinoline or partially hydrogenated isoquinoline in the presence of a ruthenium catalyst at a temperature of 110° C. to 230° C. under a hydrogen pressure of at least 10 kg/cm$^2$·G.

12 Claims, No Drawings

PROCESS FOR PRODUCTION OF DECAHYDROISOQUINOLINE

BACKGROUND OF THE INVENTION

1. Field of the Invention

This invention relates to a process for the production of decahydroisoquinoline, and more particularly to a process for the production of decahydroisoquinoline by the hydrogenation of isoquinoline or partially hydrogenated isoquinoline.

2. Description of the Prior Art

Decahydroisoquinoline is destined to find growing utility as raw material for medicines and agricultural pesticides.

As means of producing decahyroisoquinoline by the hydrogenation of isoquinoline, the method using platinum oxide as a catalyst and the method using Raney nickel as a catalyst for the hydrogenation have been known to the art.

The method which uses platinum oxide as the hydrogenation catalyst is impracticable because the platinum oxide itself is too expensive to permit commercial production of decahydroisoquinoline and the method which uses Raney nickel as the hydrogenation catalyst entails a disadvantage that the hydrogenation readily produces 1,2,3,4-tetrahydroisoquinoline, produces decahydroisoquinoline with difficulty, and yields by-products in large amounts.

The inventors continued a diligent study directed to elucidation of the causes for the drawbacks experienced to date and development of a process capable of producing decahydroisoquinoline advantageously. We have consequently found that use of a ruthenium catalyst as a hydrogenation catalyst permits economic production of decahydroisoquinoline. This knowledge has led to perfection of the present invention.

SUMMARY OF THE INVENTION

An object of this invention is to provide a process for advantageously producing decahydroisoquinoline by hydrogenating isoquinoline or partially hydrogenated isoquinoline.

Another object of this invention is to provide a proces for producing decahydroisoquinoline by hydrogenating isoquinoline or partially hydrogenated isoquinoline in the presence of a ruthenium catalyst under the conditions of 110° C. to 230° C. of reaction temperature and at least 10 kg/cm$^2 \cdot$G of hydrogen pressure. A further object of this invention is to provide a process for advantageously producing decahydroisoquinoline by using inexpensive coal tar isoquinoline which is obtained by fractional distillation or other similar means the tar bases extracted from coal tar oil or liquefied oil of coal with an acid.

DETAILED DESCRIPTION OF THE INVENTION

This invention is directed to a process for producing decahydroisoquinoline by hydrogenating isoquinoline or partially hydrogenated isoquinoline in the presence of a ruthenium catalyst under the conditions of 110° C. to 230° C. of reaction temperature and at least 10 kg/cm$^2 \cdot$G of hydrogen pressure.

The isoquinoline to be used as the raw material in this invention may be synthetic isoquinoline. Preferably, it is the isoquinoline fraction of a boiling point of 240° C. to 245° C. obtained by the precision extraction from coal tar oil or liquefied oil of coal with an acid. Desirably, this fraction is concentrated to at least 90%, preferably at least 95%, of purity.

In this invention, when synthetic isoquinoline or refined coal tar isoquinoline or partially hydrogenated isoquinoline is used as the raw material, it is hydrogenated in its unmodified form in the presence of a ruthenium catalyst to produce decahydroisoquinoline.

When crude coal tar isoquinoline which has not been sufficiently refined is used as the raw material, this raw material is desired to be desulfurized before it is subjected to hydrogenation. This is because the ruthenium catalyst to be used in the hydrogenation of isoquinoline by nature suffers its catalytic activity seriously impaired when the raw material containes sulfur.

Generally, crude coal tar isoquinoline contains, as impurities, such basic substances as quinoline, quinaldine, 8-metylquinoline, and alkyl pyridines and also sulfur-containing compounds usually in a concentration of about 0.1 wt% to 0.5 wt% of total sulfur (as sulfur). The sulfur-containing compounds present as impurities on the order of this concentration heavily poisons the ruthenium catalyst, although the presence of other impurities is tolerated by the catalyst.

This desulfurization of the crude isoquinoline is desired to be carried out until the ratio of desulfurization exceeds 90% or until the total sulfur content of the isoquinoline falls below 100 ppm, desirably below 10 ppm, and more desirably below 2 ppm by weight.

This invention does not particularly discriminate the desulfurization of crude isoquinoline by the method adopted therefor. Generally, however, the method which resorts to recrystallization and/or washing of crystalline isoquinolinium salt, the method which effects hydrogenation desulfurization in the presence of a hydrogenation catalyst such as nickel, the method which effects desulfurization in the presence of Raney nickel or other similar metal capable of reacting with sulfur, or a suitable combination of these methods is desirably adopted.

Specifically, the first method which resorts to recrystallization and/or washing of crystalline isoquinolinium salt produces highly desulfurized isoquinoline, by causing crude isoquinoline to be reacted upon by an acid capable of reacting with isoquinoline and consequently producing crystalline isoquinolinium salt, refining the isoquinolinium salt so produced by recrystallization and/or washing, and decomposing the refined isoquinolinium salt with an alkali.

Examples of the acid to be used advantageously in this case include mineral acids such as hydrochloric acid, nitric acid, perchloric acid, hydrobromic acid, sulfuric acid, and phosphoric acid and organic acids such as oxalic acid and o-pthalic acid. The refining of the crystalline isoquinolinium salt by recrystallization and/or washing is specifically effected by carrying out only the recrystallization once or more, by carrying out only the washing once or more, by carrying out the recrystallization and the washing in combination, or by carrying out the recrystallization and/or washing in an ordinary manner while using a solvent capable of dissolving the crystalline isoquinolinium salt. Examples of the solvent advantageously used in this case include alcohols such as methanol, ethanol, n-propanol, and isopropanol and aqueous solutions of such alcohols. As the alkali for the aforementioned decomposition with an alkali, there may be used, for example, an aqueous NaOH solution, an aqueous KOH solution, or aqua ammonia which exhibits stronger basicity than isoquinoline.

The second method which effects desulfurization by hydrogenation carries out the desulfurization by hydrogenating the crude isoquinoline under the pressure of hydrogen in the presence of a hydrogenation catalyst. In this case, the hydrogenation of isoquinoline may proceed to the level of 1,2,3,4-tetrahydroisoquinoline.

As the hydrogenation catalyst in this hydrogenation for desulfurization, a platinum-group type catalyst containing a platinum-group metal, such as ruthenium or platinum or a compound of the metal, is not used but a non-platinum-group type catalyst containing a non-platinum-group metal, such as nickel, molybdenum, or cobalt or a compound of the metal, is used. A nickel catalyst containing elemental nickel, such as Raney nickel or stabilized nickel, is used advantageously. The amount of the nickel catalyst to be used is desired to fall in the range of 5% to 20% based on the amount of isoquinoline under treatment.

As regards the conditions of the hydrogenation in the method of hydrogenation for desulfurization, where there is used a catalyst containing elemental nickel, the reaction temperature falls generally in the range of 70° C. to 250° C., preferably 100° C. to 230° C., the hydrogen pressure which may be normal pressure when there is sufficient supply of hydrogen ($H_2$) for the decomposition of sulfur-containing compounds is desired to exceed at least 10 kg/cm$^2$·G and the reaction time is generally at least five hours. This hydrogenation is desired to be carried out until at least 1 mole, preferably 2 to 4 moles, of hydrogen is absorbed per mole of isoquinoline. It is also desired to be carried out until at least 90% of isoquinoline is converted into tetra hydroisoquinoline. The third method which effects the desulfurization in the presence of a metal capable of reacting with sulfur treats the crude isoquinoline in the presence of a metal of large surface area, such as Raney nickel or powdered nickel, at a temperature in the range of 50° C. to 230° C. Examples of the metal which effectively reacts with sulfur compounds are nickel, iron, and cobalt. Nickel is preferably over the other metals. Raney nickel is used particularly advantageously. Since Raney nickel or other metal in this case is not expected to discharge any catalytic function, it may be adopted in the form of a spent catalyst. The reaction is desired to be carried out in the atmosphere of a gas inactive against the metal, e.g., hydrogen gas or an inert gas such as nitrogen gas.

Now, as concerns the suitable combination of the methods described above, although these methods may be combined in any desired manner, the combination of the first method and the second method or the combination of the first method and the third method proves particularly desirable.

In the combination of the first method and the second method, the first method, if used first to effect removal of at least 50%, preferably at least 90%, of the sulfur-containing compounds present in the crude isoquinoline and the resultant partially refined isoquinoline, is thoroughly desulfurized by hydrogenation in the presence of a non-platinum-group type catalyst. In this case, the first method is desired to effect the desulfurization until the total sulfur content is lowered to 10 to 500 ppm, desirably to 30 to 300 ppm, preferably to 50 to 200 ppm, and the second method to further the desulfurization until the total sulfur content falls below 10 ppm, preferably below 2 ppm. In this way, the loss of isoquinoline during the treatment of the first method can be minimized and the amount of the hydrogenation catalyst of the second method can be notably decreased. In the case of a nickel catalyst, for example, the amount of the catalyst to be used can be lowered to the level of 0.5 to 10%, preferably 2 to 7% by weight, based on the amount of isoquinoline under treatment. In the combination of the two methods under discussion, the conditions of treatment by the first method may be the same as those described above. As regards the latter treatment by the second method, the conditions may be the same as those described above except for the amount of the hydrogenation catalyst.

In the combination of the first method and the third method, the first method is first used to effect desulfurization until the total sulfur content falls to the level of 10 to 500 ppm, and then the third method is used to effect further desulfurization in the presence of a metal such as Raney nickel capable of reacting with sulfur until the total sulfur content falls below 10 ppm, preferably below 1 ppm. Also in this way, the yield of isoquinoline can be improved and the consumption of metal can be decreased.

In any of the aforementioned methods of desulfurization, the desulfurization ratio is determined by analyzing the desulfurized isoquinoline by suitable means such as, for example, gas chromatography. As the index for this analysis, use of thieno-(3,2-b)-pyridine proves convenient. The crude isoquinoline or the partially hydrogenated isoquinoline which has been desulfurized, as described above, is put to use in the subsequent step of hydrogenation either in its unaltered form or after undergoing distillation.

The hydrogenation of isoquinoline or partially hydrogenated isoquinoline is carried out in the presence of a ruthenium catalyst as the hydrogenation catalyst. The ruthenium catalyst to be used in this hydrogenation is that which has elemental ruthenium or a ruthenium compound deposited on a carrier, such as activated carbon, alumina or diatomaceous earth. Preferably, an elemental ruthenium-carried catalyst produced by impregnating a carrier with an aqueous solution of ruthenium chloride or a ruthenic acid salt and reducing the impregnated carrier with hydrogen is used.

The amount of this ruthenium catalyt to be used in the hydrogenation is in the range of 0.01 to 5.0% by weight, preferably 0.02 to 1.0% by weight, as elemental ruthenium based on the amount of isoquinoline or partially hydrogenated isoquinoline under treatment. If this amount is less than 0.01% by weight, the hydrogenation does not proceed as smoothly as desired. If the amount exceeds the upper limit, then the stirring of the reaction mixture is obtained with difficulty while the reaction velocity may be improved.

As concerns the ruthenium catalyst, the catalyst having ruthenium deposited on a carrier can be used by itself as a matter of course. Optionally, this catalyst may be used in combination with some other hydrogenation catalyst such as, for example, a nickel catalyst using Raney nickel or stabilized nickel. Alternatively, the nickel catalyst which has been used during the course of the desulfurization by hydrogenation may be left remaining in the reaction mixture and the ruthenium catalyst subsequently added to that reaction mixture. The ruthenium catalyst can be used repeatedly in successive cycles of the hydrogenation. Especially when isoquinoline or partially hydrogenated isoquinoline to be used as the raw material has been desulfurized until the total sulfur content falls below 10 ppm, preferably below 1 ppm, the ruthenium catalyst can be used repeatedly in several cycles, occasionally in ten or more cycles, of the hydrogenation.

The hydrogenation of isoquinoline or partially hydrogenated isoquinoline by the use of this ruthenium catalyst can be carried out by any of the methods known to the art, such as by the use of an autoclave or by passing isoquinoline or partially hydrogenated isoquinoline through a reaction vessel packed with a bed of this catalyst. Concerning the reaction conditions involved in this case, the reaction temperature is in the range of 110° C. to 230° C., desirably 120° C. to 190° C., and preferably 130° C. to 170° C. and the hydrogen pressure is at least 10 kg/cm$^2$·G, desirably at least 50 kg/cm$^2$·G, and preferably at least 100 kg/cm$^2$·G. If the reaction temperature and the hydrogen pressure are lower than the respective lower limits of the ranges mentioned above, the reaction time is elongated proportionately and, in the extreme case, the hydrogenation fails to proceed. If they exceed the upper limits of the aforementioned ranges, the reaction entails decomposition of ring structure and the yield is lowered. As regard the reaction time, the hydrogenation is conducted until the absorption of hydrogenation terminates, ordinarily. Generally, the reaction time is not less than five hours. Preferably, the hydrogenation is continued until the amount of hydrogen absorbed totals at least 4.5 times, desirably 5.1 times, the equivalent mole of isoquinoline. In the case of the partially hydrogenated isoquinoline, the hydrogenation is desired to be carried out until the amount of hydrogen absorbed totals at least 1.02 times the theoretical equivalent mole of the partially hydrogenated isoquinoline.

After the hydrogenation is completed, the ruthenium catalyst is separated from the reaction mixture by such means as decantation or filtration and the produced decahydroisoquinoline is isolated from the reaction mixture by such means as distillation. The ruthenium catalyst so recovered may be put to use, when necessary, in subsequent cycle of the hydrogenation.

In accordance with the process of this invention, decahydroisoquinoline of high purity can be produced in high yield economically from isoquinoline or partially hydrogenated isoquinoline as the raw meterial.

DESCRIPTION OF THE PREFERRED EMBODIMENTS

Now, the process for the production of decahydroisoquinoline by the present invention will be described more specifically below with reference to working examples. In working examples, a percent(%) describes a percent by weight.

EXAMPLE 1

To 709 g (5.3 moles) of crude isoquinoline (purity 97% and total sulfur content 0.3%) which had been isolated from the tar bases resulting from the extraction of coal tar oil with an acid, 595 g (5.6 moles) of concentrated hydrochloric acid was added dropwise with stirring and cooling. The reaction mixture so obtained was left reaction for 30 minutes. The resultant reaction mixture was distilled under a vacuum to expel water and produce a grayish white solid. This solid was recrystalized from a mixed solvent consisting of 8 parts of isopropanol and 2 parts of methanol. Consequently, needle crystals of isoquinoline chloride having a melting point of 187° C. to 189° C. were obtained. The refined isoquinoline chloride was dissolved in water and decomposed with an aquenous 20% KOH solution to liberate isoquinoline. The resultant solution was distilled to obtain 120 g of desulfurized isoquinoline (purity 99.9% and total sulfur content 1 ppm).

In an autoclave, 120 g (0.93 mol) of the aforementioned desulfurized isoquinoline 6 g of 5% ruthenium-carbon (Ru/C) catalyst were subjected to hydrogenation at a temperature of 180° C. under a hydrogen pressure of 140 kg/cm$^2$·G for 60 hours. The total amount of hydrogen absorbed during the reaction was 4.9 moles and the molar ratio of the absorbed hydrogen to isoquinoline was 5.3. The reaction mixture obtained after separation of the catalyst by filtration was analyzed by gas chromatography. It was found to contain 88% of decahydroisoquinoline. By distilling this reaction mixture, 98 g (76% in yield) of decahydroisoquinoline (197° C. to 210° C. fraction) was obtained. The trans/cis ratio of this decahydroisoquinoline was found to be 6/4.

EXAMPLE 2

In an autoclave, 1.2 kg of crude isoquinoline (purity 96% and total sulfur content 0.5%) and 180 g of stabilized nickel catalyst (N-113, produced by Japan Gasoline Chemical Co., Ltd.) were subjected to hydrogenation at a temperature of 180° C. under a hydrogen pressure of 135 kg/cm$^2$·G for 5 hours. The total amount of hydrogen absorbed during this reaction was 29.9 moles and the molar ratio of the hydrogen absorption (by molar ratio based on raw material) was 3.22. By the analysis with a gas chromatograph provided with FPD highly sensitive to sulfur compounds, the peak (total sulfur content 5 ppm) of sulfur compounds was confirmed to have substantially disappeared from the hydrogenation product.

The aforementioned reaction mixture was separated by filtration. In an autoclave, 975 g of the filtrate and 18.5 g of a 5% Ru/C catalyst were subjected to hydrogenation at a temperature of 180° C. under a hydrogen pressure of 115 kg/cm$^2$·G for 20 hours. At the end of the hydrogenation, the amount of hydrogen absorbed was 29.6 moles, the ratio of hydrogen absorption (by molar ratio based on raw material) was 4.04, and the decahydroisoquinoline content of the reaction mixture was 87.3%.

EXAMPLE 3

In an autoclave, 1.2 kg of the same crude isoquinoline as used in Example 2 and 60 g of the aforementioned stabilized nickel catalyst were subjected to hydrogenation at a temperature of 180° C. under a hydrogen pressure of 127 kg/cm$^2$·G for 21 hours. The amount of hydrogen absorbed during this hydrogenation was 17.1 moles and the molar ratio of the hydrogen absorption (by molar ratio based on raw material) was 1.84. In the analysis with a gas chromatograph, a peak of sulfur compound indicative of about 20 ppm of total sulfur was confirmed.

The aformentioned reaction mixture was filtered. In an autoclave, 1.0 kg of the filtrate and 50 g of the aforementioned stabilized nickel catalyst were subjected to hydrogenation at a temperature of 180° C. under a hydrogen pressure of 123 kg/cm$^2$·G for 14 hours. The amount of hydrogen absorbed was 0.7 mole and the ratio of hydrogen absorption (by molar ratio based on raw material) was 0.09. By the analysis with a gas chromatograph, formation of 1,2,3,4-tetrahydroisoquinoline and disappearance of the peak of sulfur compounds were confirmed.

The aforementioned reaction mixture and 40 g of a 2% Ru/C catalyst added thereto were subjected to reaction at a temperature of 180° C. under a hydrogen pressure of 140 kg/cm$^2$·G for 20 hours. The amount of hydrogen absorbed was 31.5 moles, the ratio of hydrogen absorption (by molar ratio based on raw material) was 4.20, and the decahydroisoquinoline content of the reaction mixture was 78.3%. The trans/cis ratio of the decahydroisoquinoline was 1/2.

EXAMPLE 4

In an autoclave, 1.2 kg of the same crude isoquinoline as used in Example 2 and 180 g of the aforementioned stabilized nickel catalyst were subjected to hydrogenation at a temperature of 180° C. under a hydrogen pressure of 135 kg/cm$^2$·G for 65 hours. The amount of hydrogen absorbed was 29.9 moles and the molar ratio of the hydrogen absorption (by molar ratio based on raw material) was 3.22. The resultant reaction mixture was separated by filtration and then distilled. Consequently, 1.1 kg of 1,2,3,4-tetrahydroisoquinoline (purity 94.6% and total sulfur content 0%) was obtained.

In an autoclave, 120 g of the aforementioned 1,2,3,4-tetrahydroisoquinoline and 2.4 g of a 5% Ru/C catalyst were subjected to hydrogenation at a temperature of 180° C. under a hydrogen pressure of 135 kg/cm$^2$·G for 91 hours. The total amount of hydrogen absorbed was 1.67 moles, the ratio of hydrogen absorption (by molar ratio based on raw material) was 1.85, and the decahydroisoquinoline content of the reaction mixture was 94.6%. The trans/cis ratio of the decahydroisoquinoline was 1/2.

EXAMPLE 5-8

(Purification of crude isoquinoline)

(No. 1)

600 g of crude isoquinoline (purity 95% and total sulfur content 0.3%) and 759.6 g of 47% hydrobromic acid were stirred and cooled to undergo reaction. After the reaction, the resultant reactin mixture was distilled to expel water and then washed twice with acetone to afford 864.1 g of isoquinolinium bromide. By recrystallizing this isoquinolinium bromide from 6,881 g of isopropanol, 471.9 g (recovery ratio 85.9%) of refined isoquinolinium bromide having a total sulfur content of 22 ppm was obtained. The refined isoquinolinium bromide was recrystallized again from 6,498 g of isopropanol. The recrystallized isoquinolinium bromide (676.6 g) was dissolved in the same volume of water and decomposed with an aqueous 20% NaOH solution. Then, 495.3 g of the resultant liberated desulfurized isoquinoline was distilled, to afford 374.73 g (recovery ratio 62.5%) of refined isoquinoline (purity 99.7% and total sulfur content less than 1 ppm) was obtained.

(No. 2)

In 900 g of toluene, 600 g of the same crude isoquinoline as used in the refining process of No. 1 above was dissolved. To the resultant solution, sulfuric acid in amounts equimolar with the isoquinoline was added to react thereon. The crystals consequently formed were separated by filtration to afford crystals of isoquinolinium sulfate. The crystals were washed with 900 g of toluene and then decomposed with an alkali by following the procedure of No. 1. Consequently, there was obtained 450 g of isoquinoline having a total sulfur content of 300 ppm. Then, the aforementioned isoquinoline and 22.5 g of Raney nickel added thereto were treated at 100° C. in an atmosphere of nitrogen for 1 hour. The resultant reaction mixture was subjected to solid-liquid separation and to simple distillation to afford 420 g of refined isoquinoline having a total sulfur contet of less than 1 ppm.

(No. 3)

The crystals of the same isoquinolinium sulfate as obtained in the procedure of No. 2 above were recrystallized once from 1,000 g of isopropanol and then decomposed with an alkali, to afford 415 g of isoquinoline having a total sulfur content of 103 ppm.

The isoquinoline and 20 g of Raney nickel added thereto were left reacting at a temperature of 140° C. under a hydrogen pressure of 15 kg/cm$^2$·G for 2 hours. The resultant reaction mixture was subjected to solid-liquid separation. At least 99% of the reaction mixture obtained above was 1,2,3,4-tetrahydroisoquinoline. And the total sulfur content of this reaction mixture was less than 1 ppm.

(Hydrogenation of isoquinoline with ruthenium catalyst)

The refined isoquinoline of 1,2,3,4-tetrahydroisoquinoline samples obtained by the desulfurization of the aforementioned crude isoquinoline were subjected to hydrogenation in the presence of a 5% Ru/C catalyst under the varying conditions indicated in Table 1. The reaction mixture consequently obtained were analyzed for composition by gas chromatography. In Comparative Experiment 1, the hydrogenation was carried out in the presence of stabilized nickel catalyst. The results are shown in Table 1.

TABLE 1

| | raw material | | | Reaction conditions | | | Composition of reaction mixture (%) | | | |
|---|---|---|---|---|---|---|---|---|---|---|
| | Method of purification | Amount used (g) | Amount of catalyst used (g) | Temperature (°C.) | Hydrogen pressure (kg/cm$^2$.G) | Reaction time (hr) | Low-boiling component | DHIQ | THIQ | High-boiling Component |
| Example No. | | | | | | | | | | |
| 5 | No. 1 | 100 | 5 | 145 | 100 | 6.5 | 0.5 | 99.0 | — | 0.5 |
| 6 | No. 2 | 100 | 5 | 145 | 25 | 96.0 | 3.0 | 87.3 | 5.6 | 4.0 |
| 7 | No. 3 | 34 | 1.7 | 180 | 100 | 3.5 | 11.3 | 65.9 | — | 22.8 |
| 8 | No. 3 | 55 | 2.8 | 160 | 100 | 4.5 | 1.4 | 96.6 | — | 2.0 |
| Comparative Experiment | | | | | | | | | | |
| 1 | No.1 | 50 | 2.5 | 200 | 100 | 6.0 | 0.1 | 26.3 | 71.1 | 0.3 |

Note: DHIQ stands for Decahydroisoquinoline and THIQ for tetrahydroisoquinoline.

COMPARATIVE EXAMPLE 2

In an autoclave, 1.2 kg of the same crude isoquinoline as used in Example 2 and 120 g of stabilized nickel catalyst were subjected to hydrogenation at a temperature of 180° C. under a hydrogen pressure of 145 kg/cm²·G for 37 hours. The amount of hydrogen absorbed during this reaction was 29.0 moles and the ratio of hydrogen absorption (by molar ratio based on raw material) was 3.11. By analysis with a gas chromatograph, the reaction mixture was confirmed to contain 98.4% of 1,2,3,4-tetrahydroisoquinoline. A peak of sulfur compounds was confirmed in this reaction mixture.

Then, the aforementioned reaction mixture and 60 g of newly added stabilized nickel catalyst were subjected to hydrogenation under the same conditions as described above for 22 hours. At this time, no absorption of hydrogen was recognized. By analysis with a gas chromatograph, disappearance of the peak of sulfur compounds was confirmed.

Then, the aforementioned reaction mixture was filtered. In an autoclave, the filtrate and 50 g of stabilized nickel catalyst were subjected to hydrogenation at a temperature of 180° C. under a hydrogen pressure of 120 kg/cm²·G for 14 hours. In this case, the amount of hydrogen absorbed was 9.6 moles and the ratio of hydrogen absorption (by molar ratio based on raw material) was 1.28. By analysis with a gas chromatograph, the reaction mixture was confirmed to contain 44.1% of unreacted 1,2,3,4-tetrahydroisoquinoline and 27.0% of decahydroisoquinoline.

What is claimed is:

1. A process for the production of decahydroisoquinoline by the hydrogenation of isoquinoline or partially hydrogenated isoquinoline in the presence of a ruthenium catalyst at a reaction temperature of 110° C. to 230° C. under a hydrogen pressure of at least 10 kg/cm²·G.

2. A process according to claim 1, wherein said partially hydrogenated isoquinoline is 1,2,3,4-tetrahydroisoquinoline.

3. A process according to claim 1, wherein said isoquinoline or partially hydrogenated isoquinoline is a product obtained by desulfurizing crude isoquinoline resulting from distillation and purification of tar bases extracted from coal tar oil or liquefied oil of coal with an acid.

4. A process according to claim 3, wherein said isoquinoline or partially hydrogenated isoquinoline is a product obtained by desulfurizing crude isoquinoline to a ratio of desulfurization of at least 90%.

5. A process according to claim 3, wherein said isoquinoline or partially hydrogenated isoquinoline is a product obtained by desulfurizing said crude isoquinoline until the total sulfur content is lowered to below 10 ppm.

6. A process according to claim 3, wherein said isoquinoline or partially hydrogenated isoquinoline is a product obtained by desulfurizing said crude isoquinoline until the total sulfur content is lowered to below 2 ppm.

7. A process according to claim 3, wherein said isoquinoline or partially hydrogenated isoquinoline is a product obtained by desulfurizing said crude isoquinoline in the presence of a nickel catalyst in an atmosphere of hydrogen gas at a temperature of 70° C. to 250° C.

8. A process according to claim 3, wherein said isoquinoline is a product obtained by causing said crude isoquinoline to be reacted upon by an acid thereby preparing a crystalline isoquinoline salt, subjecting said isoquinolinium salt to recrystallization and/or washing, and subsequently subjecting the recrystallization and/or washing product to decomposition with an alkali.

9. A process according to claim 3, wherein said isoquinoline is a product obtained by causing said crude isoquinoline and Raney nickel added thereto to be thermally treated.

10. A process according to claim 3, wherein said isoquinoline is a product obtained by causing said crude isoquinoline to be reacted upon by an acid thereby preparing crystalline isoquinolinium salt, subjecting the isoquinolinium salt to recrystallization and/or washing, decomposing the recrystallization and/or washing product with an alkali thereby effecting removal of at least 50% of the total sulfur content, and thereafter hydrogenating the resultant isoquinoline in the presence of a nickel catalyst until the total sulfur content is lowered to below 10 ppm.

11. A process according to claim 1, wherein said ruthenium catalyst is separated from the reaction mixture and put to use again in the subsequent cycle of hydrogenation.

12. A process according to claim 1, wherein said ruthenium catalyst used in the hydrogenation is in the amount of 0.01 to 5.0% by weight as elemental ruthenium based on the amount of isoquinoline under treatment; and wherein said isoquinoline or partially hydrogenated isoquinoline is a product obtained by the desulfurizing crude isoquinoline to a ratio of desulfurization of at least 90% and until the total sulfur is lowered to below 10 ppm; said product being obtained by desulfurizing crude isoquinoline, obtained from distillation and purification of tar bases extracted from coal tar oil or liquefied oil of coal, by reaction with an acid, resulting in a crystalline isoquinoline salt; subjecting said isoquinoline salt to recrystallization and/or washing; and subsequently subjecting the recrystallization and/or washing product to decomposition with an alkali.

* * * * *